(12) United States Patent
Kuriyama et al.

(10) Patent No.: US 6,827,902 B1
(45) Date of Patent: Dec. 7, 2004

(54) BIOCHEMICAL ANALYZER

(75) Inventors: Hiroyuki Kuriyama, Tokyo (JP); Atsushi Katayama, Kodaira (JP); Hiroshi Mitsumaki, Mito (JP); Peter Hohmann, Arese (IT)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/284,862

(22) PCT Filed: Oct. 23, 1996

(86) PCT No.: PCT/JP96/03084
§ 371 (c)(1),
(2), (4) Date: Apr. 22, 1999

(87) PCT Pub. No.: WO98/18009
PCT Pub. Date: Apr. 30, 1998

(51) Int. Cl.[7] .............................................. G01N 21/00
(52) U.S. Cl. ............................ 422/65; 422/63; 422/99; 436/47; 436/48; 436/46
(58) Field of Search ............................. 422/63, 65, 64; 436/43, 47, 48, 49; 312/194, 195, 196

(56) References Cited

U.S. PATENT DOCUMENTS

| | | | |
|---|---|---|---|
| 4,039,286 A | * | 8/1977 | Keller et al. .............. 23/230 R |
| 4,168,004 A | * | 9/1979 | Owen ......................... 209/545 |
| 4,798,423 A | * | 1/1989 | LaCour ...................... 312/195 |
| 4,965,049 A | * | 10/1990 | Lillig et al. ................ 422/68.1 |
| 5,087,423 A | * | 2/1992 | Ishibashi ..................... 422/67 |
| 5,207,986 A | * | 5/1993 | Kadota et al. ................ 422/65 |
| 5,232,081 A | * | 8/1993 | Kanamori ................. 198/465.2 |
| 5,380,488 A | * | 1/1995 | Wakatake ..................... 422/65 |
| 5,855,847 A | * | 1/1999 | Oonuma et al. .............. 422/64 |
| 5,864,138 A | * | 1/1999 | Miyata et al. ............... 250/311 |
| 5,928,952 A | * | 7/1999 | Hutchins et al. .............. 436/50 |
| 6,337,050 B1 | * | 1/2002 | Takahashi et al. ............ 422/63 |

FOREIGN PATENT DOCUMENTS

| | | | |
|---|---|---|---|
| JP | 63217273 | | 9/1988 |
| JP | 63217273 A | * | 9/1988 |
| JP | 3285174 A | * | 12/1991 |
| JP | 5264558 | | 10/1993 |
| JP | 10253635 A | * | 9/1998 |
| JP | 1183864 A | * | 3/1999 |
| JP | 20009738 A | * | 1/2000 |

* cited by examiner

Primary Examiner—Jill Warden
Assistant Examiner—Sam Siefke
(74) Attorney, Agent, or Firm—Antonelli, Terry, Stout & Kraus, LLP

(57) ABSTRACT

A biochemical analyzer for automatically analyzing components of a specimen, in which a specimen rack conveying part, a specimen introducing part, and a specimen storage part are arranged, independent from one another. The specimen introducing part, the analyzing part and the specimen storage part are coupled to one another along the longitudinal direction of the specimen conveying part. The heights of these three parts measured from the floor are from 850 to 950 mm, their depths are from 750 to 800 mm and their widths are multiples of the dimension of the specimen rack. A uniform appearance is achieved by having standardized dimensions. Also a low height provides better viewing and a lighter environment.

8 Claims, 9 Drawing Sheets

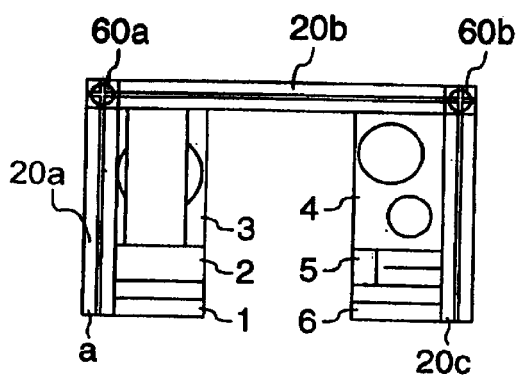
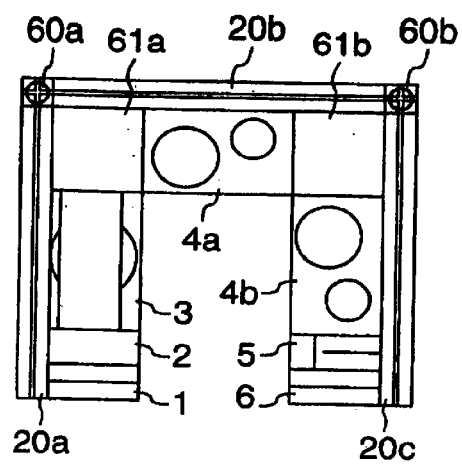
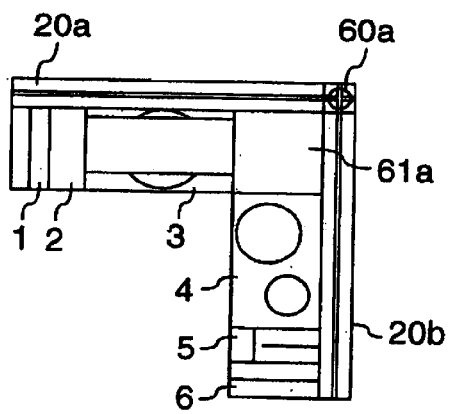
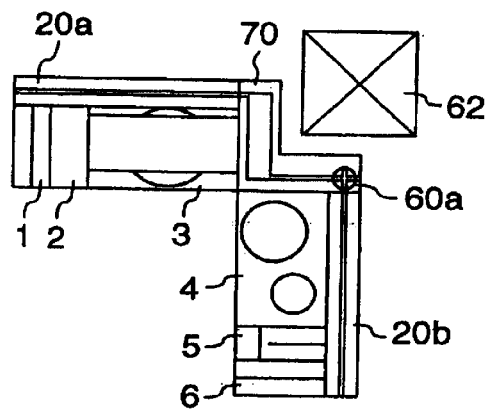
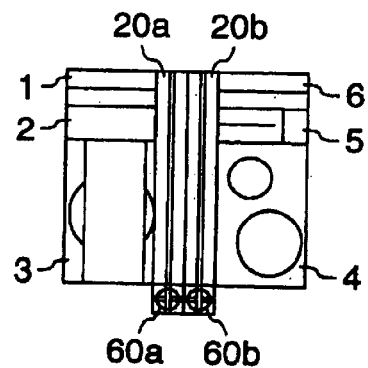

BIOCHEMICAL ANALYZER

BACKGROUND OF THE INVENTION

The present invention relates to a biochemical analyzer which can automatically carry out a series of operations including supply of specimens, and conveyance, analysis and storage thereof in a clinical analyzing apparatus for biochemically analyzing or immuno-analyzing blood, urine or the like.

Related Art

There has been well-known a conventional automatic biochemical analyzer comprising a specimen introducing part for introducing a specimen rack on which specimens are set, a specimen storage part for storing therein specimens for which analysis has been completed, the specimen introducing part being arranged at one end of the analyzer and the specimen storage part being arranged at the other end thereof, and a plurality of analyzing parts which are combined in accordance with a use purpose, and which are laid on a straight line between the specimen introducing part and the specimen storage part.

It is noted that a specimen rack conveying part for conveying the specimen rack is arranged on the rear side of the specimen introducing part, the analyzing parts and the specimen storage part, being integrally incorporated therewith, and accordingly, the specimen introducing part, the analyzing parts and the specimen storage parts are indirectly coupled with one other by means of the specimen rack conveying part.

Further, Japanese Patent Unexamined Publication No. 03-28517 discloses such an automatic analyzer that coupling parts for coupling the specimen rack conveying part with the specimen introducing and storage parts and the analyzing parts, are provided between the specimen introducing part and an analyzing part adjacent thereto, between adjacent analyzing parts, and an analyzing part adjacent to the specimen storage part and the latter, the outside dimensions and inside dimensions of the coupling parts are different from each other so as to allow the automatic analyzer to have an L- or U-like configuration, whereby distances by which laboratory technicians (including specialists and others) move, and a space in a room in which the biochemical analyzer is arranged, are effectively used.

However, in the above-mentioned conventional biochemical analyzer which is arranged in such a configuration other than a straight line configuration, the whole floor area of the biochemical analyzer is increased since the coupling parts are provided. Further, since it can be arranged in any of configurations other than a straight line configuration, an examination room having a short straight line distance can be installed, and accordingly, there can been proposed a biochemical analyzer which does not require a large-sized examination room so as to effect space saving. However, there has not yet been proposed enhancement of the environment of the examination room and the convenience requested by the technicians.

Meanwhile, in a usual examination room, a plurality of analyzing parts as mentioned above, have various sizes and shapes since inspection items and processing speeds are different from one another, and the heights of the analyzing parts are set to be higher than the height of the view points of women who cannot therefore look around the examination room in its entirety.

Further, in such a case that the shortening of examination times and the addition of inspection items are required, additional analyzing parts should be built up in an original biochemical analyzer, and if a biochemical analyzer becomes old, the analyzer should be replaced with new one. As a result, analyzing parts and peripheral equipment having various sizes are arranged in disorder.

Thus, the space of the examination room becomes small and uncomfortable, and has a dark atmosphere, that is, there has been such a problem that the environment of the examination room becomes worse.

With the provision of a single analyzer in an examination room, no serious problem occurs. However, with the provision of several analyzers coupled with one other in the examination room, the analyzer themselves exhibit the environment of the examination room in part, and accordingly, the environment of the examination room which serves as a life space for laboratory technicians gives a serious problem in working efficiency.

Further, in the case of the arrangement of a plurality of analyzers, it is impossible to easily recognize, at glance, where a specific analyzer is arranged, that is, unnecessary visual elements are present for the laboratory technicians so as to hinder rapid and sure examination.

Further, even though the biochemical analyzer can automatically carry out a series of operations such as supply, conveyance, analysis and storage of specimens, the laboratory technicians have to carry out adjustment for a sampling mechanism, replacement of components or the like, replenishment of reagents, and confirmation for operating conditions of the analyzer. In order to carry out the above-mentioned works for such an arrangement in which analyzing parts having housings of different sizes, and working surfaces of different heights, the laboratory technicians have to set their sights too high or crouch down, accordingly, simplicity and rapidness are hindered, thereby there has been a problem such that the processing capability of the biochemical analyzer cannot be fully utilized.

Further, in such a case that any one of a plurality of analyzing parts fails, the examination has to be inevitably stopped until repairing thereof is completed, even though the examination does not use the analyzing part in failure, since a specimen rack conveying part is incorporated with each of the analyzing parts.

Further, in such a case, due to failure, wearout or old style, any one of a plurality of analyzing parts has to be replaced with new one, the attachment of a new analyzing part requires the positioning of the specimen rack conveying part, and the positioning of the housing of the analyzing part.

Moreover, if the position of arrangement of an analyzing part to be replaced, is present between the specimen introducing part and the specimen storage part, the other analyzing parts have to be shifted with the use of either the specimen introducing part or the specimen storage part as a reference point, accordingly, much and heavy labor and long time are required for the replacement.

SUMMARY OF THE INVENTION

The present invention is devised in view of the above-mentioned problems of the present invention, and accordingly, an object of the present invention is to provide an automatic biochemical analyzer which can provide a safe and clean environment, and which can maintain a high degree of reliability, and which can exhibit within the examination room such a working environment that the technicians can hold his comfortable feeling of tension, and the management therefore can be made in order.

Further, another object of the present invention is to provide an automatic analyzer in which arranged analyzing parts exclude unnecessary elements, that is, only have required elements so as to exhibit an existential quantifier, and the laboratory technicians can rapidly and precisely confirm specified parts, and can rapidly discrete a situation so as to rapidly cope with the situation.

Further, another object of the present invention is to provide an automatic biochemical analyzer in which not only distances by which the laboratory technicians move can be shortened, but also dimensions with which the laboratory technicians can carry out a series of operations in a reasonable posture can be set, thereby it is possible to reduce physical fatigue, and which can always carry out safe and precise examination even in a long working time.

According to the present invention, the longitudinal dimension of the specimen rack is used as a basic dimension, the widthwise dimensions of the specimen introducing part and the specimen storage part are set to values which are multiples of the longitudinal dimension of the specimen rack, and the analyzing parts are coupled with one another through the intermediary of the specimen rack conveying parts.

Accordingly, the external dimensions can be standardized so that respective equipment can be harmonized so as to exhibit sensation of unity, and human's sensory function can be controlled so as to exhibit a comfortable environment for the laboratory technicians.

Further, another object of the present invention is to provide an automatic biochemical analyzer in which the standardization of the external dimensions are effective for common use of components, and the replacement of a component with new one is simple while its expandability is flexible.

Further, the user's areas which are provided in analyzing parts, for allowing the laboratory technicians to confirm and perform analysis have a uniform height which is lower than that of the view points of the laboratory technicians.

Thus, components in the examination room have a uniform low height so that the examination can be looked around in the examination room in its entirety, thereby it is possible to provide a bright and broad environment for the laboratory technicians.

Further, component parts which the laboratory technicians usually manipulate, and for which a periodical maintenance has to be made, are made to be noticeable by colors and shapes, so as to be visually distinguished from other parts.

Accordingly, there can be provided an automatic biochemical analyzer in which the laboratory technician can recognize at a glance where a specific component is present, even in such a case that not less than two analyzing parts are arranged, whereby it is possible to exhibit a feeling of safety and a feeling of intimacy for the laboratory technicians.

BRIEF DESCRIPTION OF THE DRAWINGS

FIGS. 9a to 9e are schematic views illustrating various configurations of biochemical analyzers according to the present invention.

DESCRIPTION OF PREFERRED EMBODIMENTS OF THE INVENTION

Detailed explanation will be hereinbelow made of the present invention in the form of preferred embodiments with reference to the accompanying drawings.

Figure 1:
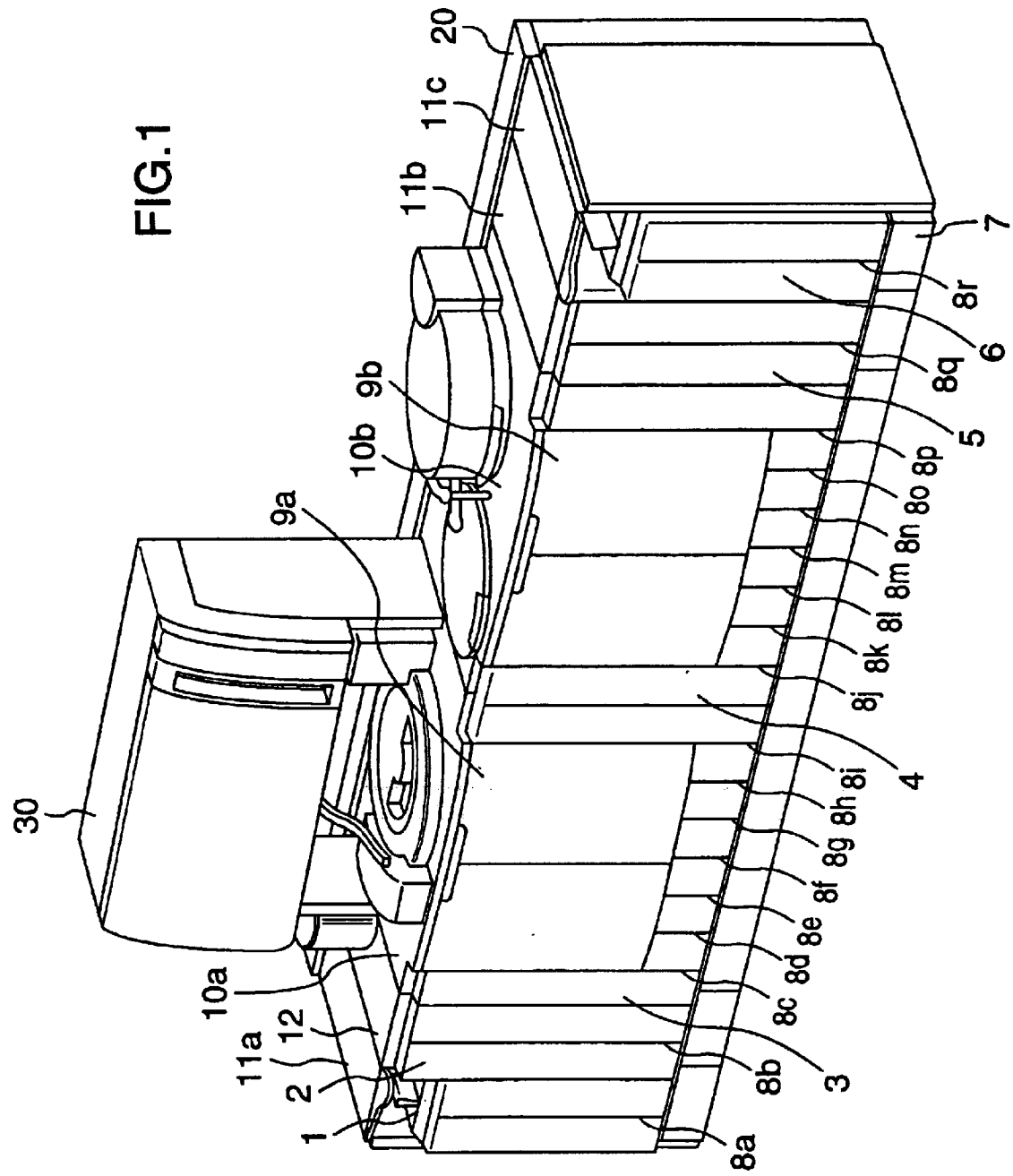
FIG. 1 is a perspective view illustrating a biochemical analyzer according to the present invention.

Referring first to FIG. 1, although a specimen rack conveying part 20, a specimen introducing part 1, an electrolyte analyzing part 2, an analyzing part 3 and an analyzing part 4, a reexamining buffer 5 and a specimen storage part 6 are shown, being separated from each other for the sake of brevity of explanation, no gaps are inherently present at positions where their housings are arranged, adjacent to one another with no gaps therebetween.

Figure 2:
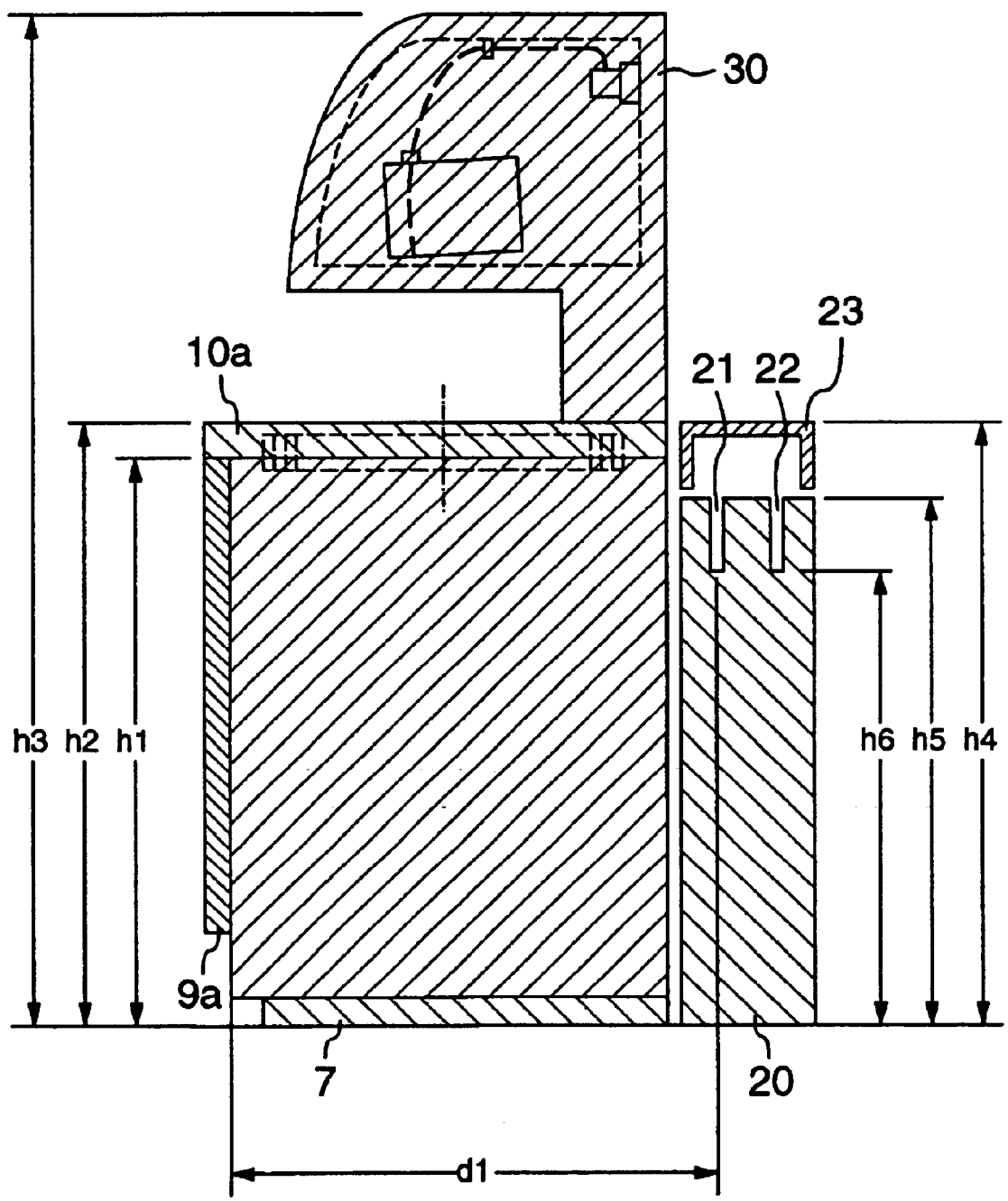
FIG. 2 is a longitudinal sectional view illustrating an analyzing part A shown in FIG. 1.
Figure 3:
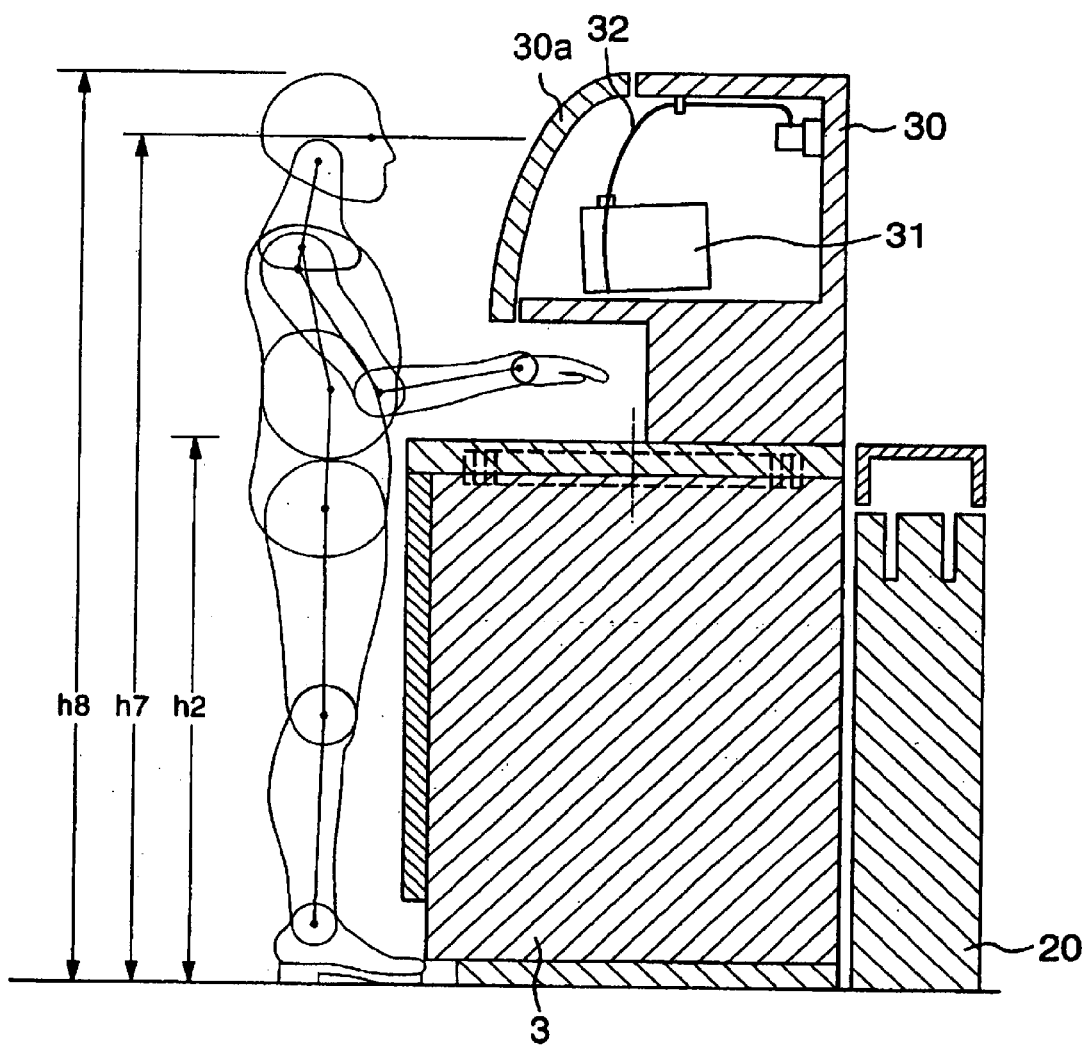
FIG. 3 is a view for explaining a relationship between the analyzing part A and the height of a worker.
Figure 4:
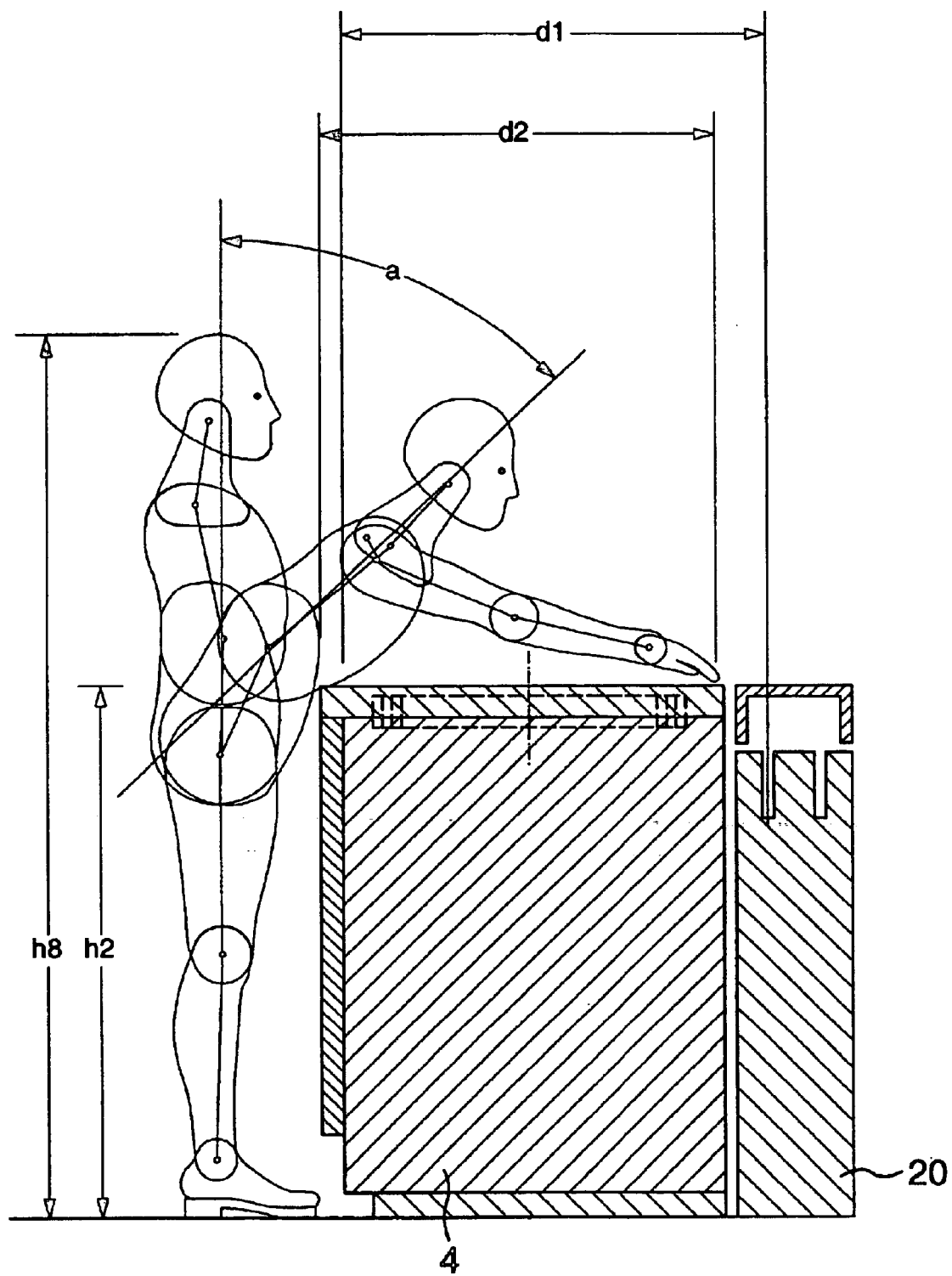
FIG. 4 is a view for explaining a working range in an analyzing part B shown in FIG. 1.
Figure 5:
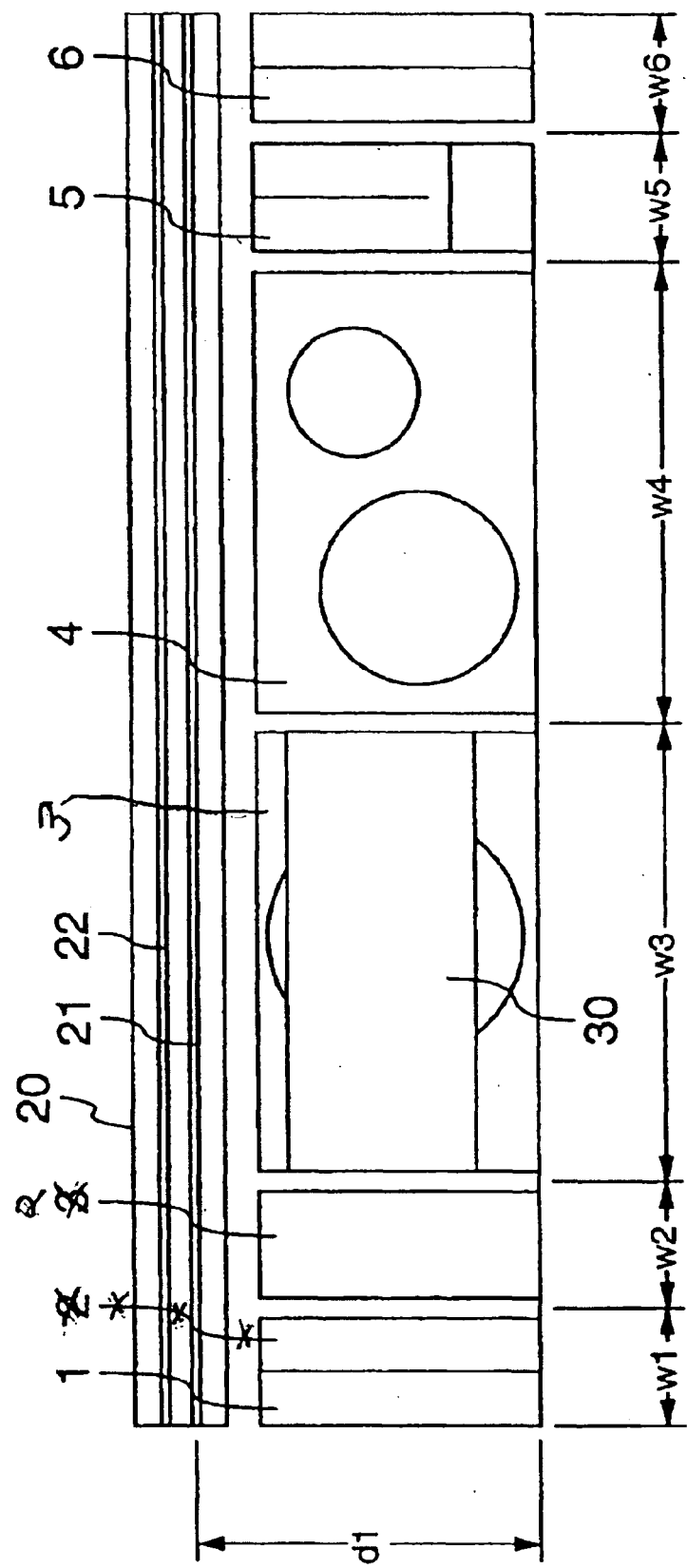
FIG. 5 is a plan view for explaining widthwise dimensions of the automatic biochemical analyzer according to the present invention.

Referring to FIGS. 1 and 2, the biochemical analyzer according to the present invention, comprises a specimen introducing part 1 for introducing a specimen rack in which specimens are accommodated, an electrolyte analyzing part 2, an analyzing part 3 provided with a reagent cold reservoir 30 projected from the top surface of a housing and having a transparent cover 30a thereof, an analyzing part 4, a reexamining buffer 5 for temporarily accommodating the specimen rack for reanalysis, and a specimen storage part 6 for accommodating therein the specimen rack for which examination is completed, they all being arranged in a one horizontal row.

The specimen introducing part 1, the electrolyte analyzing part 2, the analyzing part 3, the analyzing part 4, the reexamining buffer 5 and the specimen storage part 6 are coupled to one another through the intermediary of a specimen rack conveying part 20 including a conveyer for conveying the specimen rack, which is laid on the rear side of them and which controls the flow of the specimen rack.

It is noted the specimen rack conveying part 20 is composed of an on-going path 21 on which the specimen rack is advanced from the specimen introducing part 1 to the specimen storage part 6, and an in-coming path 22 on which the rack is advanced in a direction reverse to that of the ongoing path. A removable transparent cover 23 is provided at the top surface of the specimen rack conveying part 20.

The abovementioned specimen introducing part 1, the electrolyte analyzing part 2, the analyzing part 3, the analyzing part 4, the reexamining buffer 5, and the specimen storage part 6 are composed of base parts 7 having one and the same shape and size, and accordingly, it is apparent that they are bundled in one unit by the base parts 7.

The analyzing part 3 carries out an analysis at a high speed so that the time for the analysis is short since the number of analyzing items is small, while the analyzing part 4 has a large number of analyzing items so that the time for the analysis is long, and accordingly, they are selectively used, depending upon the content of an analysis.

Further, slits 8a to 8r are formed in the front surface sides of the respective components as mentioned above with a dimensional unit serving as a base of the widthwise dimensions of the components.

With this arrangement, even in a system in which not less than two independent analyzers are arranged in conformity with an examination facility, the dimensions of the respective analyzers are normalized being well-ordered, and functioning stations are arranged in the order of working steps by means of the base parts 7 and the slits 8 provided in the respective analyzers, thereby it is possible to exhibit the appearance of the system as a continuous and integral device.

It is noted that the above-mentioned slits 8a to 8r are shown in the form of grooves in this embodiment, they should not be limited to these grooves, but instead thereof, beads projected from the housings, or color strips having smooth surfaces may be used if they can visually and continuously recognized.

Further, the slits 8a to 8r may be in a combination of grooves, beads and color strips.

Further, function identification parts 9a, 9b for indicating analyzing parts where a specimen is added therein with a reagent so as to analyze components of the specimen are formed on the front surface sides of the analyzing parts 3, 4, and stages 10a, 10b for exhibiting user's zones includes a part where a laboratory technician opens and closes the cover, prepares and adjusts a sample probe or the like, and replaces consumable things such as reagents, and a control part for instructing manipulations which are not shown.

With the provision of the above-mentioned identification parts 9a, 9b, in a biochemical analyzing system in which not less than two standardized analyzers are arranged, the laboratory technician can soon recognize at a glance where a specific component is located, at any position which is far from a particular analyzer, or near thereto, thereby it is possible to prevent the view point from being uselessly moved or displaced.

Further, with the provision of the stages 10a, 10b, a part the technician has directly touch, can be instantly recognized.

It is noted that there are shown the function identification parts 9a, 9b which are concave shapes projected respectively from the housings of the analyzing parts. However, they should not be limited to such shapes, but they may be concave shapes or smooth color surfaces if they can be visually distinguished from other parts. Further, although the above-mentioned stages are provided as separate members on the top surfaces of the respective analyzing parts, the present invention should not be limited to this arrangement, but they may be those which are colored parts directly applied to the top surfaces of the respective analyzing parts.

If the stages 10a, 10b can be exhibited in combination with colors, the parts can be easily distinguished from others, and accordingly, the laboratory technician can instantly and precisely recognize the presence thereof so as to exhibit higher technical effects.

Explanation will be hereinbelow made of external dimensions of the apparatus according to the present invention.

The height h1 of an analyzing part 3 is set to be in a range from 850 to 920 mm while a height H2 of the stages 10a is set to be in a range from 850 to 950 mm, and the height h3 of the reagent cold reservoir 30 is set to be in a range from 1,350 to 1,650 mm.

Further, the inward depth d2 of the analyzing part 3 is set to be in a range from 650 to 750 mm. The forward side depth d1 of the specimen rack conveying part 20, measured from the center position of the on-going path 21 is set to be in a range from 750 to 800 mm.

It is noted that the height and depth of the analyzing part 4, and the height of the stage 10b are the same as those of the analyzing parts 2 as mentioned above although they are not shown in detail.

Further, the specimen introducing part 1, the reexamining buffer 5 and the specimen storage part 6 are provided with covers 11a, 11b, 11c, instead of stages 10a provided in the analyzing part 3, and the electrolyte analyzing part 2 is provided with a top panel 12, instead of the stage 10b. In this arrangement, the heights of the specimen introducing part 1, the reexamining buffer 5 and the specimen storage part, and the heights of the covers 11a, 11b, 11c and the top panel 12 are the same as those explained as to the analyzing part 3.

Further, as to the heightwise dimensions of the specimen rack conveying part 20, the height h4 of the cover 23 provided to the specimen rack conveying part 20 is set to be in a range from 850 to 950 mm, and the overall height h5 of the specimen rack conveying part 20 is set to be in a range from 760 to 950 mm in view of such a fact that the height of the specimen rack is 70 mm, and the specimen rack conveying part 20 is not projected from the top surface of the analyzing part 3. Further, a height h6 of a conveyer line which is not shown, is set to be 690 to 790 mm.

Since Japanese adult women have an averaged height h8 of 1,580 mm, and since the height h7 of their view points is a 1,460 mm, the overall height of the biological analyzing apparatus is standardized in a range from 850 to 9.50 mm, as mentioned above, and accordingly, the height of the biologically analyzing apparatus is set to be lower than the height of the view point of the laboratory technician.

If an object which is higher than the view point of the user himself is present, apprehension is felt, and accordingly, the space is recognized to be narrower than that actually obtained. However, if the examination room can be looked around in its entirety, the human's sensory function can be controlled so that the space can be recognized to be bright and broad.

As a result, a comfortable environment can be provided so as to reduce the mental apprehension in order to alleviate the fatigue even in a long time examination work, thereby it is possible to take concentration on the examination work.

Since the depthwise dimensions of the apparatus is uniformed, no protrusions and recesses are present on the front and rear sides of the device, no useless floor area is present, and accordingly, it is possible to aim at saving the space. Further, since the external appearance is continuous with no external protrusions and recesses visual noises can be reduced.

Further, in the automatic biological analyzer having the above-mentioned dimensions, if a Japanese adult woman takes a standing posture as well as a reasonable forward tilting posture at a tilting angle of less than 30 deg., the depth d2 by which her hands can reach by stretching her arms, is in a range of 700 to 800 mm.

Thus, the hands can reach up to the center position of the on-going path 21 of the specimen rack conveying part 20 with a reasonable posture.

Accordingly, even if an abnormality occurs in the specimen rack conveying part 20 laid on the most inward side during examination, the hands can reach a require part without changing the working posture and without taking an unreasonable posture, thereby it is possible to safely and rapidly carry out the examination work.

It is noted that the reagent cold reservoir 30 provided in the analyzing part 3, is accommodated therein with a reagent container 31 containing therein a reagent solution which is fed into the analyzing part 3 through a reagent tube 32.

In the front surface part of the reagent cold reservoir 30, an opening having a top surface depth and a bottom surface depth which is larger than the former, is formed, and the opening is covered with an opening and closing transparent cover 30a defining a curved surface.

The above-mentioned reagent cold reservoir 30 has a height h3 which is in a range of 1,350 to 1,650 mm, and accordingly, the remaining quantity of the reagent solution in the reagent container 31 can be confirmed easily at a position which is lower than the view point of a Japanese adult woman. Alternatively, it can be easily confirmed by slightly upward directing her glance.

Further, even a person who is taller than Japanese adult women having an averaged height, can easily confirm the remaining quantity of the reagent solution in the reagent container 31 by obliquely downward directing his glance.

Further, since the opening and closing cover 33 has a curved surface, even though condensation occurs in the cover 33, no water droplets drop into the reagent container 31.

Next, explanation will be made of the widthwise dimensions of the components in this embodiment of the present invention.

According to the present invention, the specimen rack on which specimens are set, is conveyed by the specimen rack conveying part 20 to the respective analyzing parts so as to automatically analyze it. Thus, widthwise dimensions of the components are set, using the longitudinal dimensions of the specimen rack as a base.

The longitudinal dimension of the specimen rack including a drive part is 150 mm, the widthwise dimensions w1, w2, w5, w6 of the specimen introducing part 1, the electrolyte analyzing part 2, the reexamining buffer 5 and the specimen storage part 6 are set to 300 mm which is a multiple of the longitudinal dimension of the specimen rack. In general, the specimen introducing part 1, the analyzing parts 3, 4 and the specimen storage part 6 have widthwise dimensions which are multiples of the longitudinal length of the specimen rack, including 1.

Further, the analyzing part 3 and the analyzing part 4 have widthwise dimensions w3, w4 is set to 1,200 mm which is a multiple of the longitudinal dimension of the specimen rack.

Further, slits at intervals of 150 mm which is the longitudinal dimension of the specimen rack are formed in the front surface sides of the specimen introducing part 1, the electrolyte analyzing part 2, the reexamining buffer 5 and the specimen storage part 6.

As mentioned above, since the heights and widths of the housing of the components are standardized, and the slits are formed at equal intervals, even in such a case that not less than two independent analyzing parts are arranged in the examination room, the analyzer can exhibit a continuous external appearance.

With this arrangement, visual noise can be reduced for the laboratory technician.

Figure 6:
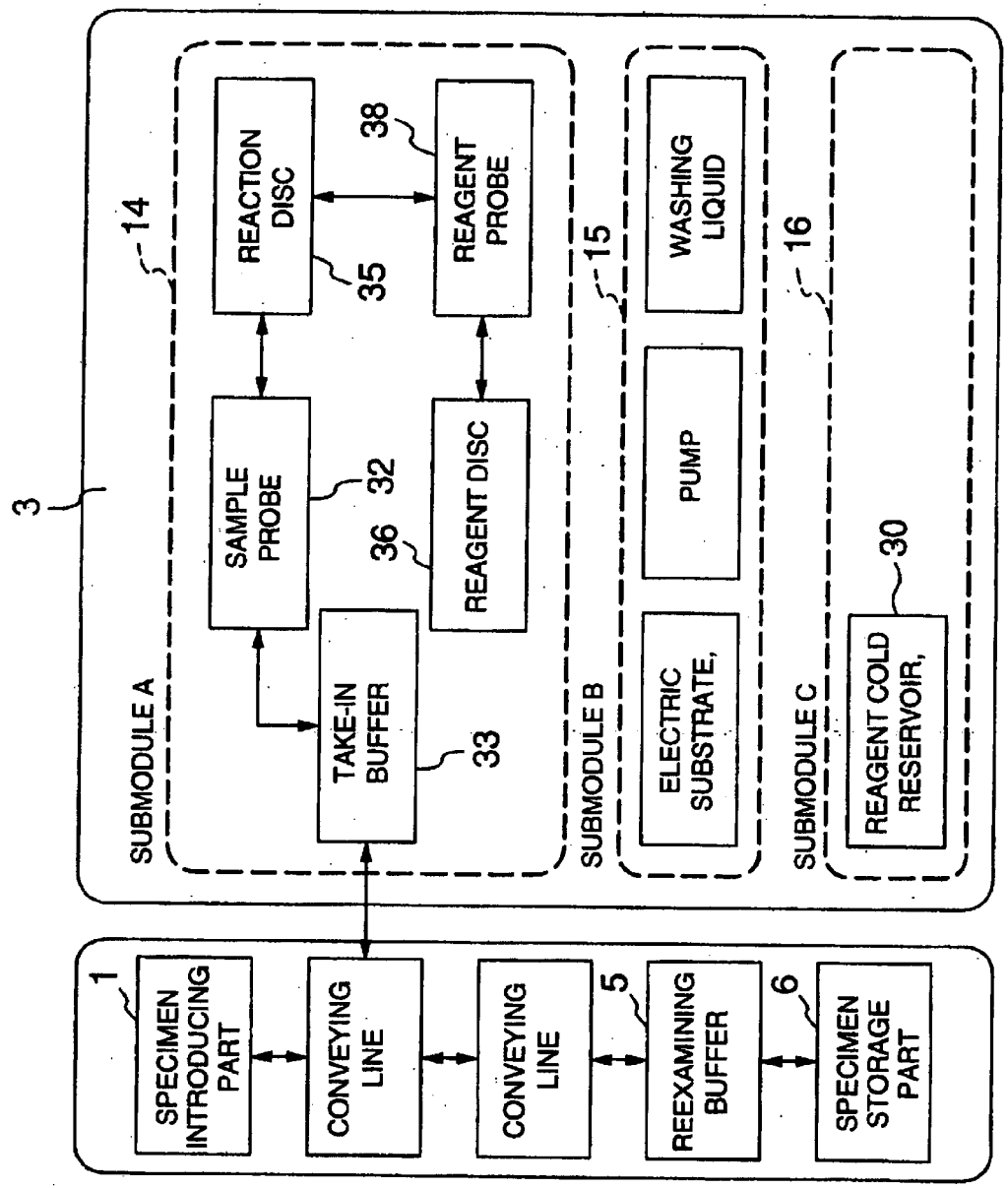
FIG. 6 is a conceptual view for explaining the relationship among structural parts of the biochemical analyzer according to the present invention.
Figure 7:
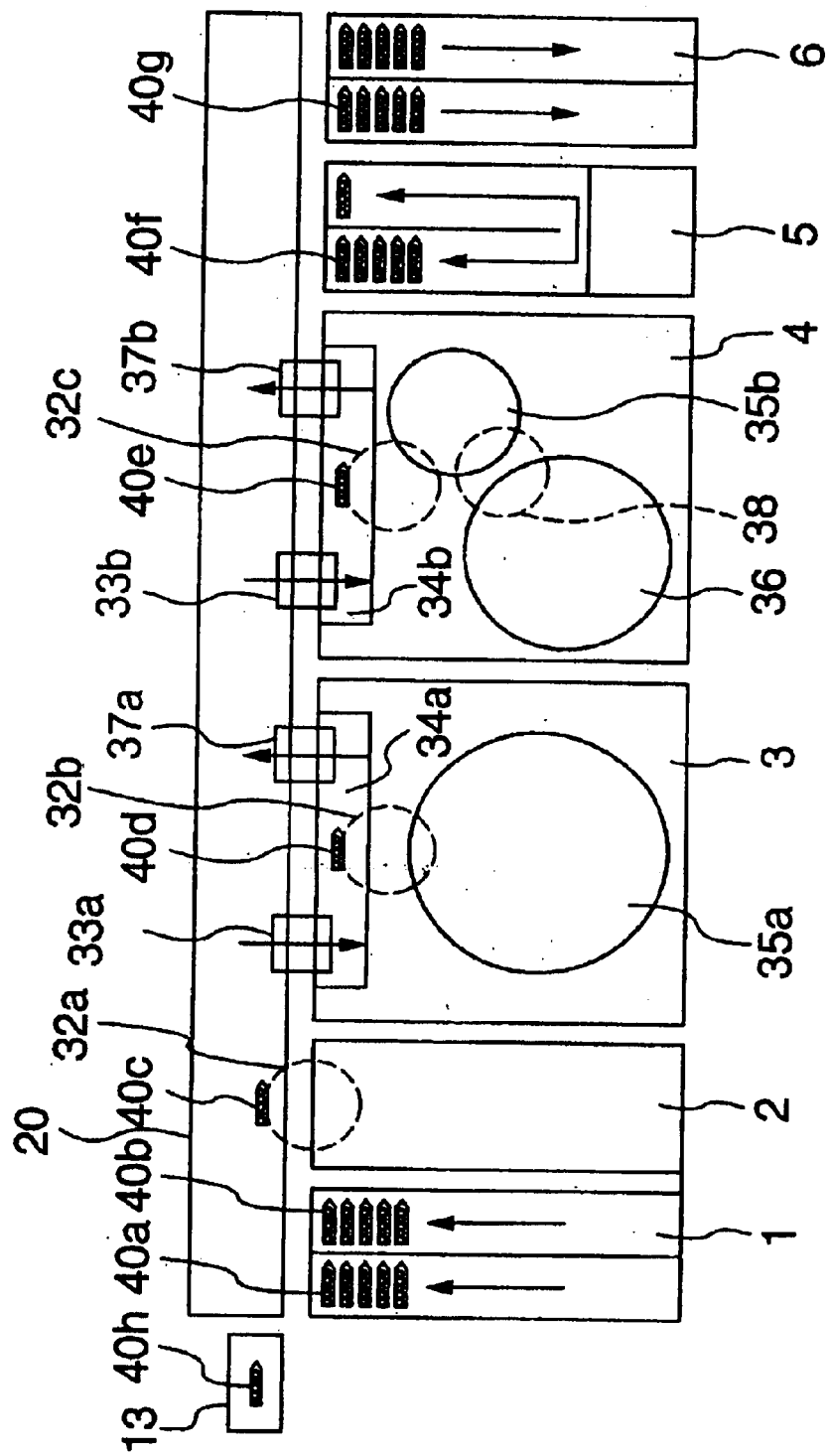
FIG. 7 is a schematic view illustrating a flow of a specimen.

Referring to FIG. 6 which is a conceptual view for explaining a relationship of the structure of the biochemical analyzer according to the present invention, and FIG. 7 which is a schematic view illustrating the flow of the specimen, the method of installation of the biochemical analyzer according to the present invention fill, and the flow of the specimen will be explained. It is noted that the arrows indicated in FIG. 6 exhibit that accuracy is required for the positional relationship between two components.

Further, if a capability of installations in the examination room and the arrangement of the biochemical analyzer according to the present invention are determined, a required length of the specimen rack conveying part 20 can be determined since the widths of the analyzing parts are standardized.

After the arrangement of the specimen rack conveying part 20 in the examination room is completed, the specimen introducing part 1, the electrolyte analyzing part 2, the analyzing part 3, the analyzing part 4, the reexamining buffer 5 and the specimen storage part are connected to the specimen rack conveying part 20.

In this arrangement, the specimen introducing part 1, the reexamination buffer 5, and a sample probe 32a in the specimen storage part 6 should be precisely connected to a conveying line provided in the specimen lack conveying part 20.

It is noted that structure of the analyzing part 3 comprises a submodule 14 composed of a take-in buffer 33, a sample probe 32, a reaction disc 35, a reagent probe 38 and a specimen rack discharge part 37, and a submodule 15 composed of an electric substrate, a pump and a washing liquid which are not shown, and a submodule 16 including the reagent cold reservoir 30.

Further, the structure of the analyzing part 4 is composed of the submodule 14 in which the reagent is added, the submodule 16 being eliminated.

In the above-mentioned arrangement, the take-in buffer 33 should have accuracy in connection with the conveying line, and the structures included in the submodule 14 should have accuracy in connection.

Then, explanation will be made of the flow of the specimen. Specimen racks 40a, 40b arranged in the specimen introducing part 1, are shifted onto the specimen rack conveying part 20, and are thereafter carried into the electrolyte analyzing part 2 having a highest frequency of reliance in clinical biochemical examination.

The above-mentioned electrolyte analyzing part 2 is provided therein with a sample probe 32 by which a sample can be directly taken out from the specimen rack 40c on the specimen rack conveying part 20.

A sample taken out from a first specimen on the specimen rack which has been stopped on the specimen rack conveying part 20, is measured by ion selective electrodes which are not shown, and the results of the measurements are outputted to a printer or a display which are not shown.

If measurement items set in the electrolyte analyzing part 2 are requested further for the first specimen, the above-mentioned sampling is repeated. Further, similar sampling is repeated for specimens subsequent to the second one. The sampling is continued until the sampling for the measurement items which are set for all specimens on the specimen rack in the electrolyte analyzing part 2 are completed.

Next, as to the specimen rack 40c for which the sampling in the electrolyte analyzing part 2 has been completed, whether measurement items set in the analyzing part 3 are requested for specimens on the specimen rack or not is determined by a computer in a control part which is not shown. If the measuring items are requested for even only one of the specimens, the specimen rack is moved to the analyzing part 3.

The take-in buffer 33a is provided in the analyzing part 3, and the specimen rack 40d is taken into the sampling part 30 from the specimen rack conveying part 20, and a sample taken out from the specimen rack 40d by a constant quantity is pipetted onto a reaction disc 35a by the sampling probe 32b. Thereafter, a predetermined quantity of a reagent is pipetted onto the reaction disc 35a by the reagent sample probe, and after the reaction by a predetermined time, the sample is measured by a photometer which is not shown, and then, the results of the measurement are outputted to a printer or a display which are not shown.

It is noted that the measurement items set in the analyzing part 3 are also requested for a specimen located at a first position, the above-mentioned sampling is repeated. Further, the same operation can be repeated for specimens subsequent to the second one, and the sampling is repeated until the sampling for all measurement items set in the analyzing part 3 for all specimens on the specimen rack is completed.

Next, as to the specimen rack for which the sampling in the analyzing part 3 is completed, whether measurement items set in the analyzing part 4 are requested for any of specimens on the specimen rack or not is determined by the computer in the control part which is not shown. If the measuring items is requested for even only one of the specimens, the specimen rack is discharged onto the specimen rack conveying part 20, by the specimen rack discharge part 37a and is carried into the analyzing part 4. After the specimen rack is carried into the sampling part 34b by the take-in buffer 33b, samples are pipetted on the reaction disc 35b, and thereafter, predetermined quantities of the reagent are pipetted onto the reaction disc 35b from the reagent set on a reagent disc 36 by a reagent probe 38. After a predetermined time elapses, the sample are measured by a photometer which is not shown, and the results of the measurements are outputted to the printer or the display which are not shown.

It is noted that the specimen rack for which the sampling is completed in the analyzing part 4 is carried to a specimen rack discharge part 37b by which it is returned to the rack conveying part 20, and is then carried to the reexamining buffer 5.

The specimen rack 40f having been carried to the reexamining buffer 5, is held therein until the analysis is completed, and then, the specimen rack with no abnormality found in the analysis is conveyed to the specimen storage part 6 under the control of the computer in the control part which is not shown.

Further, the specimen rack with an abnormality found in the analysis is returned onto the specimen rack conveying part 20 by which it is conveyed again to the associated analyzing parts so as to repeat the above-mentioned analysis.

Further, an emergency specimen introducing part 13 is present in the left upper end part of the specimen introducing part 1. If a specimen rack 40h is set in the emergency specimen introducing part 13 while a specimen rack is present in the specimen introducing part 1, the specimen rack 40h is carried onto the specimen rack conveying part 20 from the emergency specimen introducing part 1, preferential to the specimen rack present in the specimen introducing part 1.

Meanwhile, after the sampling in the electrolyte analyzing part 2 is completed, if no more measurement items set in the analyzing parts 3, 4 are requested, the specimen rack is carried to the specimen storage part 6 on the specimen rack conveying part 20, and is then stored in the specimen storage part 6.

Further, after the sampling in the electrolyte analyzing part 2 is completed, and further after the sampling in the analyzing part 3 is completed, if no measurement items set in the analyzing part 4 are requested, the specimen rack is carried to the specimen storage part 6 by the specimen rack conveying part 20, and is stored in the specimen storage part 6.

As mentioned above, since the specimen rack conveying part 20 is independent from the other components, even though any one of the plurality of analyzing parts fails, if the analysis can be made in any other analyzing part, it is not necessary to completely stop the analysis.

Figure 8:
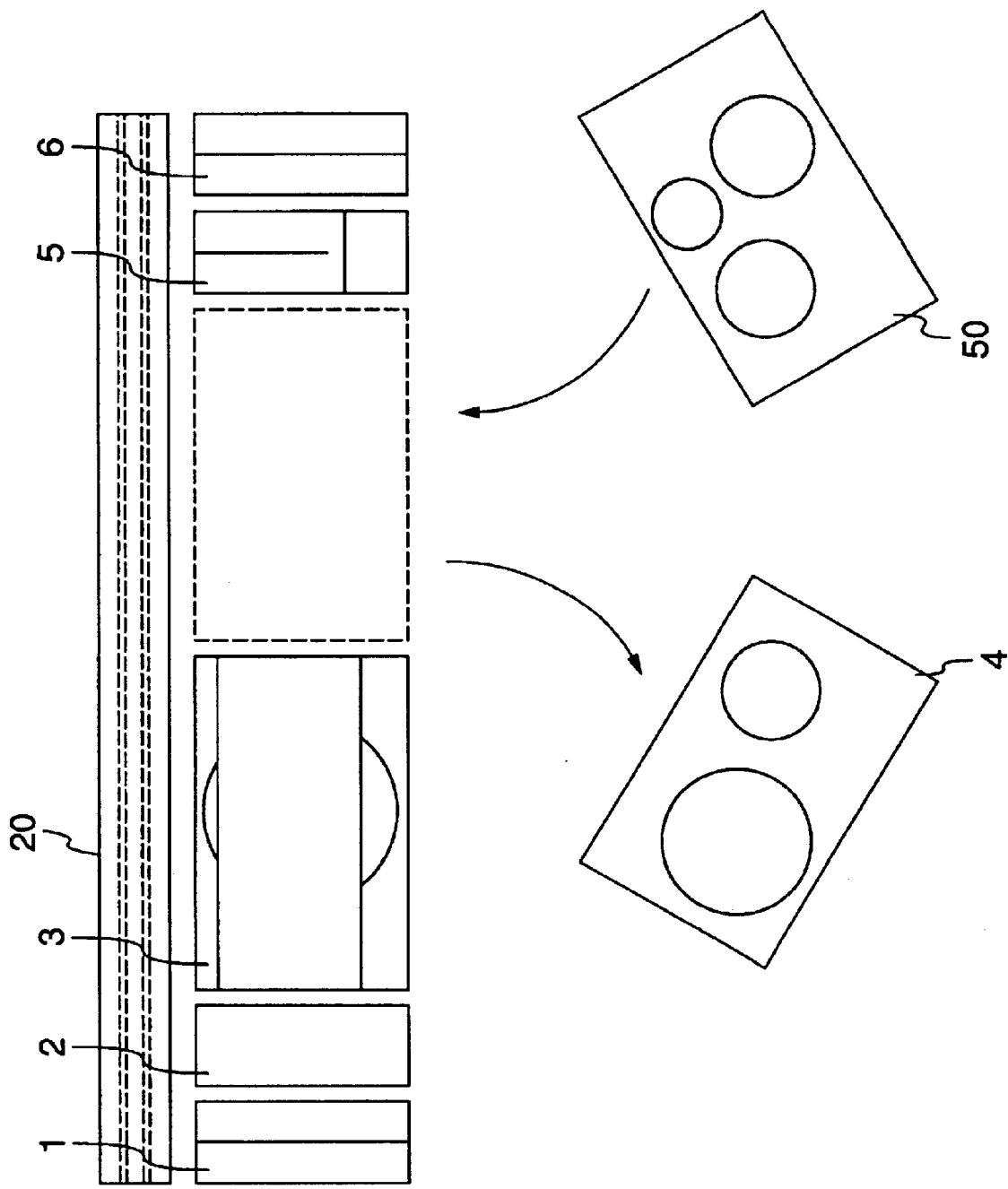
FIG. 8 is a schematic view for explaining a replacement of analyzing parts.

FIG. 8 is a schematic view for explaining the replacement of analyzing parts. The dimensions of the automatic analyzer according to the present invention is standardized as mentioned above, and further, the respective analyzing parts are coupled to one another by the specimen rack conveying part 20.

In view of this fact, if, for example, the analyzing part 4 fails, becomes deteriorated, or malfunctions so that it has to be replaced, the analyzing part 4 is removed from the specimen rack conveying part 20, and a new analyzing part 50 is inserted in a space formed by the removal of the analyzing part 4, and is connected with the specimen rack conveying part 20. Accordingly, the replacement can be made simply and shortly with no displacement of the other components.

Although it has been explained that all components are arranged on one straight line along the specimen rack conveying part 20 in this embodiment, the arrangement of the components can be simply changed only by changing the configuration of the specimen rack conveying part 20.

FIGS. 9a to 9e show other configurations of the biochemical analyzer according to the present invention. It is noted that like reference numerals are used to denote like parts which have explained in FIGS. 1 to 8.

Referring to FIG. 9a, specimen rack conveying parts 20a, 20b, 20c are arranged in a U-like shape, and rotors 60a, 60b for changing the advancing direction of the specimen rack 40 are arranged between the specimen rack conveying part 20a and the specimen rack conveying part 20b and between the specimen rack conveying part 20b and the specimen rack conveying part 20c. Further, the specimen introducing part 1 and the specimen storage part 6 and the components located between therebetween are arranged along the specimen rack conveying part 20a, 20b, 20c laid in the U-like shape.

Referring to FIG. 9b, specimen rack conveying parts 20a, 20b, 20c are arranged in a U-like shape, and rotors 60a, 60b for changing the advancing direction of the specimen rack 40 are arranged between the specimen rack conveying part 20a and the specimen rack conveying part 20b and between the specimen rack conveying part 20b and the specimen rack conveying part 20.

Further, corner tables 61a, 61b are arranged between the specimen rack conveying part 20a and the specimen rack conveying part 20b and between the specimen rack conveying part 20b and the specimen rack conveying part 20c. These corner tables 61a, 61b may be used as setting beds for peripheral units used for the examination work, and further, they may be used as an accommodation bed for consumable parts or the like.

Further, the specimen introducing part 1 and the specimen storage part 6 and the component parts therebetween are arranged along the specimen rack conveying part 20a, 20b, 20c arranged in the U-like shape.

The configurations shown in FIGS. 9a and 9b can be applied in an examination room having a relatively short direct distance. Further, since a working space can be obtained between apparatuses arranged therein, that is, the analyzers are opposed to each other with the working space therebetween. Thus, a large number of components can be monitored simultaneously, and further the distance by which the laboratory technician moves, can be shortened.

In particular, on the side on which the thus arranged analyzer is opened, the specimen introducing part 1 and the specimen storage part 6 can be opposed to each other, and accordingly, the distance by which the laboratory technician moves can be shortened.

Referring to FIG. 9c, specimen rack conveying parts 20a, 20b are arranged in an L-like shape, and a rotor 60a for changing the advancing direction of the specimen rack 40 is arranged between the specimen rack conveying part 20a and the specimen rack conveying part.

Further, the specimen introducing part 1 and the specimen storage part 6 and the components therebetween, are arranged along the specimen rack conveying part 20a, 20b arranged in the L-like shape.

According to the configuration shown in FIG. 9c, the analyzer can be arranged in an examination room having a relative short direct distance, and at each corner of an examination room, and a large number of components can be monitored simultaneously. Accordingly, the distance by which the laboratory technician moves, can be shortened.

Referring to FIG. 9d, a bent L-like module 70 is arranged in order to change the advancing direction of the specimen rack into a direction perpendicular thereto, and a specimen rack conveying part 20a and a specimen rack conveying part 20b are arranged at opposite ends of the bent module 70, respectively.

Further, a rotor 60a for changing the advancing direction of the specimen rack 40 is arranged between the specimen rack conveying part 20a and the specimen rack conveying part 20b.

In this bent module 70, the specimen rack carried by the specimen rack conveying part 20a is slid onto the analyzing part 3, and when the specimen rack reaches a corner of the bent module 70 on the analyzing part 3, the specimen rack is slid onto the rotor 60a in the bent module 70a although such an arrangement is not shown.

In a general hospital building in which posts 62 having a size of 600 to 1,000 mm are arranged in each span (6000 mm), the configuration shown in FIG. 9d can be arranged with no interference with the posts 62. Thus, it is possible to effectively use the installation space.

Referring to FIG. 9e, specimen rack conveying part 20a and specimen rack conveying part 20b are arranged in a back-to-back relation, and rotors 60a, 60b for changing the advancing direction of the specimen rack 40 are arranged between the specimen rack conveying part 20a and the specimen rack conveying part 20b.

Further, the specimen introducing part 1 and the specimen storage part 6 and the components therebetween are arranged along the specimen rack conveying part 20a, 20b arranged in the back-to-back relation.

With the configuration shown in FIG. 9e, the analyzer can be arranged in an examination room having a short direct distance, thereby it is possible to aim at saving the installation space in the examination room.

Although it has been explained that the biochemical analyzer according to the present invention is composed of the specimen introducing part, the electrolyte analyzing part 2, the analyzing part 3, the analyzing part 4, the reexamining buffer 5, the specimen storage part and the specimen rack conveying part 20, several kinds of analyzing parts, the same kind of analyzing parts or the combination thereof may be selected in accordance with a kind of an examination facility.

Further, although not shown, a preprocessing device such as a centrifugal separator, a specimen stocker as a peripheral unit may be combined with the above-mentioned analyzer.

What is claimed is:

1. A biochemical analyzer for automatically analyzing a specimen, comprising;

a specimen introducing part for introducing a specimen rack;

a specimen rack conveying part having an ongoing straight path and an incoming straight path which are substantially straight over their allover lengths, for reciprocally conveying the specimen rack introduced from the specimen introducing part, to and from at least two analyzing parts having different functions and having substantially equal widths, for pipettng specimens on the specimen rack and allowing the specimens to react with reagents so as to analyze the specimens, through the ongoing straight path and the incoming straight path;

a reexamining buffer for temporarily storing the specimen rack for reanalysis; and a specimen storage part for storing the specimen rack for which the pipetting is completed, the analyzing parts having the different functions, the reexamining buffer being located between the specimen introducing part and the specimen storage part in line, the specimen introducing part, the analyzing parts having the different functions, the reexamining buffer and the specimen storage part being coupled to one another in rear of them by the outgoing straight path and the incoming straight path, the specimen introducing part, the specimen rack conveying part, the analyzing parts, and the specimen storage part being independent from one another and being arranged on a floor so that each of them is independently removable, and the specimen introducing part, the analyzing parts, the reexamining buffer and the specimen storing part having heights measured from the floor, which are substantially equal to one another, and depths which are substantially equal to one another, wherein the specimen rack conveying part conveys the specimen rack introduced by the specimen introducing part to any of the analyzing parts, and the reexamining buffer, and also conveys the specimen rack to be reexamined from the reexamining buffer to any of the analyzing parts under the control of a control part for controlling conveyance of the specimen rack.

2. A biochemical analyzer as claimed in claim 1, wherein the specimen introducing part, the rack conveying part, the analyzing parts and the specimen storage part have heights which are set in a range of 850 to 950 mm measured from floor surface on which the biochemical analyzer is installed, and depths which are set in a range of 750 to 800 mm.

3. A biochemical analyzer for automatically analyzing a specimen, comprising:

a specimen introducing part for introducing a specimen rack;

a specimen rack conveying part having an ongoing straight path and an incoming straight path which are substantially straight over their overall lengths, for reciprocally conveying the specimen rack introduced from the specimen introducing part, to and from at least two analyzing parts having different functions through the oncoming straight path and the incoming straight path, the analyzing parts pipetting a specimen on the specimen rack and allowing the specimen to react with a reagent so as to analyze the specimen;

a reexamining buffer for temporarily storing the specimen rack for reanalysis;

a specimen storage part for storing the specimen rack for which the pipetting is completed, the analyzing parts and the reexamining buffer being arranged between the specimen introducing part and the specimen storage part in line, and being coupled to one another by the outgoing straight path and the incoming straight path in rear of the analyzing parts and the reexamining buffer, the specimen introducing part, the specimen rack conveying part, the analyzing parts and the specimen storage part being removable, independent from one another, and the specimen introducing part, the analyzing parts, the reexamining buffer, and the specimen storage part having widthwise dimensions which are multiple of the longitudinal length of the specimen rack, including 1, wherein the specimen rack conveying part conveys the specimen rack to any of the analyzing parts, the reexamining buffer and the specimen rack storage part, and also conveys the specimen rack to be reexamined from the reexamining buffer to any of the analyzing parts under the control of a control part for controlling conveyance of the specimen rack.

4. A biological analyzer as claimed in claim 1, further comprising function identification parts arranged to indicate the analyzing parts where a specimen is added with a reagent so as to analyze components of the specimen, wherein function identification parts have concave shapes projected respectively from the analyzing parts.

5. A biochemical analyzer as claimed in claim 1, wherein stages are provided on the top surface sides of at least the analyzing parts, at positions where an operator carries out confirmation, adjustment and replacement during specimen analysis.

6. A biochemical analyzer as claimed in claim 1, wherein said specimen rack conveying means comprises said ongoing straight path and said incoming straight path accommodated in a housing, for conveying the specimen rack in different directions.

7. A biochemical analyzer as claimed in claim 1, wherein each of the analyzing parts includes a take-in buffer and a specimen rack discharge part through which the specimen rack is introduced therein an is discharged therefrom.

8. A biochemical analyzer as claimed in claim 5, wherein said specimen introducing part and the specimen storage part have covers laid at the same height as that of the stages provided to the analyzing parts, measured from the floor.

* * * * *